United States Patent [19]

Tur

[11] 4,331,655
[45] May 25, 1982

[54] COSMETIC COMPOSITIONS AND PROCESSES CONTAINING ETHER AND ACYL DERIVATIVES OF 3,7,11-TRIMETHYL-2,6,10-DODECATRIENE-1-OL

[75] Inventor: Wladimir Tur, Mutschellen, Switzerland

[73] Assignee: Uni-Chemie AG, Volketswil, Switzerland

[21] Appl. No.: 71,796

[22] Filed: Sep. 4, 1979

[51] Int. Cl.³ .............. C11D 3/48; A61K 7/42; A61K 7/44
[52] U.S. Cl. .............. 424/59; 252/106; 424/60; 424/63; 424/64; 424/70; 424/358; 424/365; 560/261; 568/687
[58] Field of Search .............. 424/59, 64, 70; 560/249, 875

[56] References Cited

U.S. PATENT DOCUMENTS 4,115,547  9/1978  Degen et al. .............. 424/59

FOREIGN PATENT DOCUMENTS 1961146  6/1970  Fed. Rep. of Germany .............. 424/59
1961152  6/1970  Fed. Rep. of Germany .............. 424/317
2602037  7/1976  Fed. Rep. of Germany .............. 424/59
1190002  3/1959  France .............. 424/47

*Primary Examiner*—Dale R. Ore
*Attorney, Agent, or Firm*—James E. Nilles

[57] ABSTRACT

Cosmetic compositions and processes for face and body comprising a cosmetologically effective amount of a compound of the formula

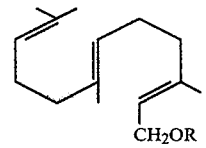

wherein R is selected from the group consisting of $C_1$-$C_4$ alkyl and $C_1$-$C_4$ acyl; and
  a cosmetologically acceptable carrier. The compositions and processes are useful in smoothing of wrinkles, normalization of skin fat and increase in moisture retaining capacity of the skin.

25 Claims, No Drawings

COSMETIC COMPOSITIONS AND PROCESSES CONTAINING ETHER AND ACYL DERIVATIVES OF 3,7,11-TRIMETHYL-2,6,10-DODECATRIENE-1-OL

BACKGROUND OF THE INVENTION

1. Field of the Invention

The present invention relates to cosmetic preparations and processes containing ether and acyl derivatives of 3.7.11-trimethyl-2.6.10-dodecatriene-1-ol.

2. Description of the Prior Art

The aim of modern cosmetic care is to delay the physical and chemical changes of the skin that take place as a consequence of ageing and of environmental influences to replenish or substitute the lacking substances, and to actively maintain the healthy state of the skin.

The natural balance and activity of the skin metabolism can be maintained by the use of specific organic agents such as biologically active substances prepared from plant material or animal material.

The sesquiterpene alcohol 3.7.11-trimethyl-2.6.10-dodecatriene-1-ol is naturally abundant, but only in small quantities. It has been known in nature for a long time, and is used in the preparation of perfumes as a component of essential oils and essences, and partly also as their accompanying substance.

It has been thought that this sesquiterpene alcohol and other compounds of similar composition would show fungicidal and bactericidal activity, but in comprehensive investigations (DE-OS No. 1'961'152) this could not be confirmed.

It has also been known that substances of similar composition to this sesquiterpene alcohol added to oils and fats do not impede transpiration when applied to the skin. Although these expectations could not be confirmed, for example 3.7.11-trimethyl-2.6.10-dodecatriene-1-ol has also been used (FR-PS No. 1'190'002).

SUMMARY OF THE INVENTION

One object of this invention is to provide a cosmetic preparation showing greater activity than known cosmetics.

Another object of the invention is to provide a cosmetic composition not having any harmful side effects on the human body.

Still a further object of the invention is to provide cosmetic compositions useful in hair-shampoos, bubble bath preparations, lipsticks, sun-protective preparations and the like.

These and other objects of the invention which will become more readily apparent can be attained by providing a cosmetic composition for face and body comprising a cosmetologically effective amount of a compound of the formula

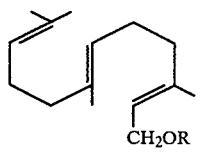

wherein R is selected from the group consisting of $C_1$–$C_4$ alkyl and $C_1$–$C_4$ acyl; and a cosmetologically acceptable carrier.

DETAILED DESCRIPTION OF THE PREFERRED EMBODIMENTS

When searching for suitable biologically active substances it was found that sesquiterpene alcohol 3.7.11-trimethyl-2.6.10-dodecatriene-1-ol which, in the form of a pyrophosphate, normally occurs only as intermediate in the metabolism of the human organism, has, in the form of its ether and acyl derivatives, cosmetically interesting properties. It was found that terpene alcohol 3.7.11-trimethyl-2.6.10-dodecatriene-1-ol derivatives from the sesquiterpene series are indeed new cosmetically active substances which, when applied to the skin, show especially cosmetically desirable effects and properties.

The preparation according to the invention is characterized therefore by a cosmetic composition for face and body comprising a cosmetologically effective amount of a compound of the formula

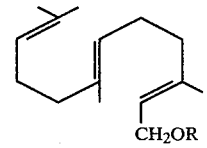

wherein R is selected from the group consisting of $C_1$–$C_4$ alkyl and $C_1$–$C_4$ acyl.

It has now been found, and was confirmed by the experiments described below, that the ether and acyl derivatives according to this invention have exactly the opposite effect to that claimed in the prior art for the corresponding alcohols: they considerably increase the capacity of the skin to retain moisture. Derivatives according to this invention have not been used in the prior art in effective concentrations in cosmetic preparations such as cremes, lotions, and the like. It was found that, surprisingly, the ether and acyl derivatives of 3.7.11-trimethyl-2.6.10-dodecatriene-1-ol when added in cosmetologically active concentrations preferably in 0.3% to 12% by weight, most preferably in 1 to 3% by weight to cosmetics such as cremes, lotions, face masks, jellies, oils, bath salts, ointments, shampoos, and the like have considerable cosmetically desirable effects such as the smoothing of wrinkles, normalization of skin fat, improvement of the mechanical properties of the skin such as its elasticity and tissue tension, and an increase of the moisture retaining capacity of the skin. Existing wrinkles are smoothed and the withered, unelastic state of the skin is clearly improved.

Most preferred are those compounds where R=$CH_2CH_3$ or R=$COCH_3$ or mixtures thereof. Among the cosmetologically acceptable carriers are those such as solvents, e.g. water, acetone, ethyl acetate, ethanol, glycols, 2.2-dimethyl-4-hydroxymethyl-1.3-dioxolane or isopropanol; or carriers in the form of a liquid emulsion, such as oil dispersion; or gels. The composition may contain either one of the compounds of this invention or mixtures thereof. The compositions may further contain swelling agents, thickening agents, emulsifiers, surface-active substances, film-forming substances, perfumes and the like. Among such compositions are shampoos, liquid complexion bases, bubble bath preparations, lipsticks, sun-protective preparations, lipbalms and liquid make-up preparations. The ether and acetate derivatives of this invention can be obtained according to one or more of the following references:

V. Heitland, "Seifen, Oele, Fette, Wachse", Volume 13, 1970;
Nowack, G. A. "Die Kosmetischen Präparate";
Beilstein, Handbook of Organic Chemistry, E. III, 1.2040;
R. A. Eckstein, "Kosmetologie" pp 4-8 (1971);
Jainstyn, H., "Handbuch de Kosmetika und Riechstoffe", Volume 3 (1973), introduction.

Having now generally described this invention, a further understanding can be obtained by reference to certain specific examples which are provided herein for purposes of illustration only and are not intended to be limiting unless otherwise specified.

Several recipes for cosmetic preparations containing 3.7.11-trimethyl-2.6.10-dodecatriene-1-ol derivatives are given in the following:

EXAMPLE 1: Night Creme W/O emulsion (preferred recipe)

A night creme was prepared having the following composition:

| | | |
|---|---|---|
| Bees' wax | 8% | by weight |
| Cholesterol | 2 | by weight |
| Softisan, Dynamit Nobel AG (Germany) | 1 | by weight |
| Wool fat | 6 | by weight |
| Arlacel 83, Atlas Chemical Ind. (USA) | 3 | by weight |
| Miglyol 812, Dynamit Nobel AG (Germany) | 15 | by weight |
| Safflower oil | 5 | by weight |
| Cetiol V, Henkel & Co. GmbH (Germany) | 5 | by weight |
| Phenonip, Nipa Lab. (England) | 0.5 | by weight |
| 3.7.11-trimethyl-2.6.10-dodecatriene-1-ol-ethyl ether | 5 | by weight |
| Perfume | 0.5 | by weight |
| Demineralized water | to 100.0 | by weight |

EXAMPLE 2: Wrinkle oil

A wrinkle oil was prepared having the following composition:

| | |
|---|---|
| PCL liquid, Dragoco (Germany) | 10% by weight |
| Olive oil | 30 by weight |
| Miglyol 812, Dynamit Nobel AG (Germany) | 22 by weight |
| Cetiol V, Henkel & Co. GmbH (Germany) | 25 by weight |
| 3.7.11-trimethyl-2.6.10-dodecatriene-1-ol acetate | 12 by weight |
| Irgasan DP 300, Ciba-Geigy AG (Switzerland) | 0.3 by weight |
| Perfume | 0.7 by weight |
| | 100% by weight |

EXAMPLE 3: Face Lotion

A face lotion was prepared having the following composition:

| | |
|---|---|
| Ethyl alcohol | 20% by weight |
| Glycerine | 5 by weight |
| Allantoin | 0.4 by weight |
| Hamamelis distillate | 5 by weight |
| Germall 115, Sutton Lab. (USA) | 0.3 by weight |
| 3.7.11-trimethyl-2.6.10-dodecatriene-1-ol acetate | 0.3 by weight |
| Demineralized water | 69 by weight |
| | 100% by weight |

EXAMPLE 4: Hair and Bath Shampoo

A hair and bath shampoo was prepared having the following composition:

| | | |
|---|---|---|
| Texapon ASV, Henkel & Co. GmbH (Germany) | 22% | by weight |
| Tween 20, Atlas Chemical Ind. (USA) | 6 | by weight |
| Lantrol AWS, Malmstrom Chem. Corp. (USA) | 3 | by weight |
| Comperlan KM, Henkel & Co. GmbH (Germany) | 2 | by weight |
| 3.7.11-trimethyl-2.6.10-dodecatriene-1-ol acetate | 2 | by weight |
| 3.7.11-trimethyl-2.6.10-dodecatriene-1-ol ethyl ether | 2 | by weight |
| Perfume | 0.5 | by weight |
| Demineralized water | to 100.0 | by weight |

3.7.11-Trimethyl-2.6.10-dodecatriene-1-ol derivatives when worked into a creme base in the above mentioned concentrations and applied to the facial skin for several days normalize the secretion of sebaceous matter: sebostatic skin becomes fatter, and seborhoeic skin becomes visibly less fat. Also the reduced capacity of the skin to retain moisture, which frequently is a consequence of excessive washing, is normalized by repeated application of a creme containing 3.7.11-trimethyl-2.6.10-dodecatriene-1-ol derivatives. In contrast to the frequently used natural Moisturizing Factor which attempts to provide substitutes for the lost body substances, genuine normalization of the moisture retaining capacity of the skin, an effect that is clearly visible and measurable, is achieved in this case by influencing metabolic processes: the skin becomes more elastic and smoother.

In keeping with the methods that are customary in modern cosmetics, the following measurements were made before and after repeated application of a night creme containing 3.7.11-trimethyl-2.6.10-dodecatriene-1-ol derivatives as described in Examples 1 and 2.

I. Measurement of wrinkle depth

The depth of wrinkles was measured by the method described by Tronnier (Parf. u. Kosm., 40, 25–29 (1959)).

Measurements were made on the forehead of the test persons. To begin with, the initial wrinkle depths were measured. Two groups of persons were treated twice daily for a fortnight: one group with the preparation according to Example 1, and the other group with the same creme base but without the added 3.7.11-trimethyl-2.6.10-dodecatriene-1-ol derivative. The following table shows the mean values of the differences in wrinkle depth after 14 days treatment:

| | |
|---|---|
| Untreated initial depth: | 33.6 |
| Creme base only: | 32.5 |
| Preparation acc. to Example 1: | 28.9 |

The above results show clearly the reduction in wrinkle depth after treatment with the preparation. The mean difference, expressed in percent of the original wrinkle depth, was approximately 14%.

II. Measurement of natural skin frequency

Measurements were made by the method described by *Tronnier and Wagener* (Dermatologica 104, 135 (1952)).

These measurements are based on the following principle: two probes are placed on the skin; one probe is excited with a variable frequency, while the intensity of the vibration of the skin is sensed by the other probe and is recorded. The resonance frequency of the entire system is lower the greater the elasticity and/or the moisture content of the skin. A lower natural frequency (negative values) corresponds, therefore, to better elasticity and/or higher moisture content of the epidermis, while a higher natural frequency (positive values) is to be regarded as a sign of reduced elasticity or of drying out.

The measurements were made on several test persons during two hours before and after application of the cosmetic preparation according to Example 1, at 15 minute intervals. The following table shows the mean difference from the initial natural frequency, in Hz:

Measurement of natural frequency

| Preparation | Initial value | Difference from initial value, Hz | | | | | | |
|---|---|---|---|---|---|---|---|---|
| | | immediately | 15' | 30' | 45' | 60' | 90' | 120' |
| Preparation according to Example 1 | 223 | −33 | −3 | −4 | −2 | −12 | −10 | −9 |
| Creme base according to Example 1 | 227 | −21 | +6 | −1 | −2 | 2− | −2 | −1 |

In contrast to the creme base of Example 1 alone, the cosmetic preparation according to Example 1 produces a pronounced increase in elasticity of the skin, which is maintained for an extended period.

III. Measurement of the moisture content of the skin

The measurements were made with the "Dermatometer" according to Bingmer, by the method described by *Winkler and Wagener* (Arch. Derm Res. 254, 287 (1975)). This instrument is based on the stray capacitor principle and permits determining the actual moisture content of the upper skin layer. Repeated measurements over several hours showed that the moisture retaining capacity of the skin has been improved by application of the preparation.

The water content of young, elastic skin is approximately 10 to 12% corresponding to 70–80 scale divisions on the measuring instrument, while the instrument reads 45–55 scale divisions for dry skin containing approximately 6% water.

Persons with dry skin were selected for the tests. The mean blank values were determined first, followed by measurements, over several hours, of skin areas treated with the preparation according to Example 1 and with the creme base only:

Mean Values of skin moisture content

| Hours: | 1 | 2 | 3 | 4 | 5 | 6 | 7 |
|---|---|---|---|---|---|---|---|
| Blank value | 56 | 57 | 57 | 58 | 58 | 57 | 56 | 56 |
| Preparation according to Example 1 | | 80 | 80 | 80 | 80 | 78 | 76 | 74 |
| Creme base according to Example 1 | | 80 | 80 | 76 | 72 | 62 | 58 | 56 |

These comparative measurements show that the preparation according to Example 1 increases the moisture content of the epidermis as well as its capacity to retain moisture.

IV. Measurement of sebaceous matter

The quantities of sebaceous matter were measured with the "Sebumeter" by the method described by Schaefer and KuhnBussius. The principle of this method consists in making a rough glass or a rough plastic foil translucent by wetting it with fat by pressing it against the skin. The degree of translucency depends on the applied quantity of fat, and is photometrically measured for determining the quantity of fat (Tronnier, Aerzt. Kosmetologie 6, 179 (1976)).

In the case of persons suffering from seborhoea it is cosmetologically desirable to normalize the secretion of sebaceous matter by the effect of suitable agents.

Persons having skin with a high fat content were selected for the test, and were treated with the preparation according to Example 1 twice daily for three weeks. The normalizing effect of preparation 1 was proven by comparison of the average initial values with the fat quantities after the treatment. The results are shown in the following table:

| | before | after |
|---|---|---|
| Preparation according to Example 1 | 48 | 25 |
| Creme base, Example 1 | 48 | 47 |
| Blank value, untreated | 48 | 47 |

It is evident from the above values that normalization of the secretion of sebaceous matter has been achieved by the application of preparation 1.

All measurements described in the foregoing clearly showed differences between the effectiveness of a creme containing 3.7.11-trimethyl-2.6.10-dodecatriene-1-ol ethyl ether and that of the same creme base but without the added agent. The observed results were: smoothing of wrinkles, improved elasticity, increased moisture content of the skin, and reduced sebaceous matter content of the fatty skin type. 3.7.11-trimethyl-2.6.10-dodecatriene-1-ol derivatives represent, therefore, a new group of skin normalizing cosmetic agents, which are suitable for use in purely cosmetic preparations as well as in bath salts, hair lotions, and the like.

| | |
|---|---|
| SOFTISAN | = LAURYL ACID TRIGLYCERIDE |
| ARLACEL 83 | = SORBITAN SESQUIOLEATE |
| MIGLYOL 812 | = CAPRYL-CAPRIN-TRIGLYCERIDE |
| CETIOL V | = DECYLOLEATE |
| PHENONIP | = P-OXY-BENZOIC ACID ESTER |

| | | |
|---|---|---|
| PCL LIQUID | = | CETARYL OCTANOATE |
| IRGASAN DP 300 | = | 5-CHLORO-2-(2,4-DICHLOROPHENOXY)-PHENOL |
| GERMALL 115 | = | IMIDAZOLIDINYLUREA |
| TEXAPON ASV | = | FATTY ALCOHOL ETHER SULFATE |
| TWEEN 20 | = | SORBITAN LAURATE |
| LANTROL AWS | = | POLYETHYLENEGLYCOL-LANOLIN DERIVATIVE |
| COMPERLAN KM | = | COCONUT OIL ACID-MONOETHANOLAMIDE |

Having now fully described this invention, it will be apparent to one of ordinary skill in the art that many changes and modifications can be made thereto without departing from the spirit or scope of the invention set forth herein.

What is claimed as new and desired to be secured by letters patent of the United States is:

1. A cosmetic composition for face and body which increases the capacity of the skin to retain moisture, comprising a cosmetologically effective amount of a compound of the formula

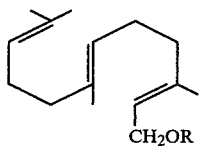

wherein R is $C_1$–$C_4$ alkyl; and
a cosmetologically acceptable carrier.

2. The composition of claim 1, wherein R is —$CH_2CH_3$.

3. The composition of claim 1 or 2 wherein said compound is present in an amount of 0.3–12% by weight.

4. The composition of claim 1 or 2 wherein said compound is present in an amount of 1 to 3% by weight.

5. The composition of claim 1, wherein said carrier is a solvent selected from the group consisting of water, acetone, ethyl acetate, ethanol, a glycol, 2.2-dimethyl-4-hydroxymethyl-1.3-dioxolane, and isopropanol.

6. The composition of claim 1, which is in the physical form of a liquid emulsion or a gel.

7. The composition of claim 1, wherein said compound is dispersed in a liquid.

8. The composition of claim 7, wherein said liquid is an oil.

9. The composition of any of claims 1, 2, 5, 6, 7 or 8, which also comprises at least one substance selected from the group consisting of "a swelling agent, a thickening agent, an emulsifier, a surface active substance, a film forming substance and a perfume".

10. The composition of claim 1, which is a hair shampoo.

11. The composition of claim 1, which comprises a liquid complexion base.

12. The composition of claim 1, which is a bubble bath preparation.

13. The composition of claim 1, which is a lipstick.

14. The composition of claim 1, which is a sun-protective preparation.

15. The composition of claim 1, which is a lip-balm.

16. The composition of claim 1, which is a liquid make-up.

17. In a cosmetologically active composition for face and body, the improvement which comprises adding thereto a cosmetologically effective amount of a compound of the formula

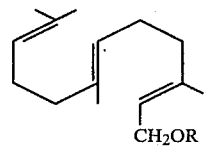

wherein R is $C_1$–$C_4$ alkyl, said amount being effective to increase the capacity of the skin to retain moisture.

18. The composition of claim 17, wherein R is $CH_2CH_3$.

19. The process of moisturizing the skin and hair which comprises treating the skin and hair with a composition comprising a cosmetically acceptable carrier and a compound of the formula:

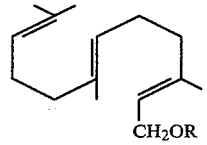

wherein R is selected from the group consisting of $C_1$–$C_4$ alkyl and $C_1$–$C_4$ acyl, in effective amount to increase the capacity of the skin and hair to retain moisture.

20. The process of claim 19 wherein R is —$CH_2CH_3$.

21. The process of claim 19 wherein R is

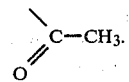

22. The process of claims 19, 20 or 21 wherein said compound is present in amount of 0.3–12% by weight.

23. The process of claim 19, 20 or 21 wherein the compound is present in amount of from 1–3% by weight.

24. The process of claim 19 wherein said carrier is a solvent selected from the group consisting of water, acetone, ethyl acetate, ethanol, a glycol, 2,2-dimethyl-1-4-hydroxymethyl-1-1,3-dioxolane and isopropanol.

25. The process of claim 19 wherein the composition also contains at least one substance selected from the group consisting of a swelling agent, an emulsifier, a surface active agent, a film forming substance and a perfume.

* * * * *